United States Patent [19]

Sharpe et al.

[11] Patent Number: 5,222,973
[45] Date of Patent: Jun. 29, 1993

[54] ENDOSCOPIC GRASPING TOOL SURGICAL INSTRUMENT

[75] Inventors: Leslie A. Sharpe, Edina, Minn.; Francis C. Peterson, Prescott, Wis.

[73] Assignee: Sharpe Endosurgical Corporation, Minneapolis, Minn.

[21] Appl. No.: 848,332

[22] Filed: Mar. 9, 1992

[51] Int. Cl.5 ............................................. A61B 17/28
[52] U.S. Cl. .................................. 606/206; 294/99.2
[58] Field of Search ............... 606/127, 128, 205–211; 128/750–755, 3–6; 294/99.2

[56] References Cited

U.S. PATENT DOCUMENTS

| | | |
|---|---|---|
| 987,173 | 3/1911 | Sale . |
| 1,274,669 | 8/1918 | Bohn .................................. 606/206 |
| 1,294,284 | 2/1919 | Logeman ........................... 606/206 |
| 2,034,785 | 3/1936 | Wappler . |
| 2,060,366 | 11/1936 | Dunlap ................................ 606/206 |
| 2,137,710 | 11/1938 | Anderson . |
| 2,549,731 | 4/1951 | Wattley . |
| 3,404,677 | 10/1968 | Springer . |
| 3,844,291 | 10/1974 | Moen . |
| 3,989,049 | 11/1976 | Yoon . |
| 4,226,239 | 10/1980 | Polk et al. . |
| 4,607,620 | 8/1986 | Storz . |
| 4,655,219 | 4/1987 | Petruzzi . |
| 4,944,741 | 7/1990 | Hasson ................................ 606/207 |
| 4,994,079 | 2/1991 | Genese et al. . |

FOREIGN PATENT DOCUMENTS 0065054 11/1982 European Pat. Off. ............. 606/205
2091624 8/1982 United Kingdom ................ 606/205

OTHER PUBLICATIONS

WISAP, "Minimal Invasive Surgery", Semm System, Instruments.
"Endoscopic Instruments", Cook Urological, A Cook Group Company.

Primary Examiner—C. Fred Rosenbaum
Assistant Examiner—William Lewis
Attorney, Agent, or Firm—Merchant, Gould, Smith, Edell, Welter & Schmidt

[57] ABSTRACT

The present invention is directed to an endoscopic grasping tool for use inside a patient. As the distal tips of the jaws come together they form a pivot point for continued jaw closure increasing the grasping force of the jaws.

7 Claims, 5 Drawing Sheets

ENDOSCOPIC GRASPING TOOL SURGICAL INSTRUMENT

BACKGROUND OF THE INVENTION

1. Technical Field

The present invention relates to surgical instruments for use during laparoscopic surgery. More particularly, the invention is directed to a grasping and clamping surgical tool for use inside the abdominal cavity.

2. Description of the Prior Art

The typical laparoscopic surgical procedure begins with the puncture of the patient's abdominal wall and the placement of an access port. Next, gas is admitted to the abdominal cavity partially inflating it, forming a pneumoperitoneum. Next a laparoscope or endoscope is inserted through the access port to permit viewing of the organs during the surgical procedure. Typically, the laparoscope has both an eyepiece for direct use by the physician and a video monitor to permit visualization of the surgical field. Additional access ports may be located elsewhere on the patient's abdominal wall to permit insertion of surgical instruments. Access ports come in a variety of diameters and 5, 7 and 11 millimeter ports are widely used for surgery within the peritoneal cavity. Instruments for insertion through such ports are readily available to practitioners and numerous surgical grasping instruments are available to surgeons specializing in these procedures. See for example:

U.S. Pat. No. 2,034,785 which teaches the use of a hinged jaw set which closes with a remote handle structure.

U.S. Pat. No. 3,404,677 also teaches the use of a jaw set. In this reference a spring is used to bias the jaw set into an open position. When the jaw set is retracted into the tube, the teeth close.

U.S. Pat. No. 4,226,239 teaches a jaw set having a single tooth on each jaw. This jaw set concentrates the closing force imparted by the jaws onto a point.

SUMMARY OF THE INVENTION

The present invention is directed to an endoscopic grasping tool which may have either forceps-type jaws or hemostat-type jaws. During jaw closure the distal tips of the jaw set closes first. At closure, this point forms a pivot point for the jaw set. Continued retraction forces the jaw set to rotate into a closed position about this distal pivot point greatly increasing the holding power of the jaw set.

BRIEF DESCRIPTION OF THE DRAWING

Throughout the several figures of the drawing like reference numerals are used to identify identical structure, wherein.

DETAILED DESCRIPTION OF THE DETAILED EMBODIMENT

Figure 1:
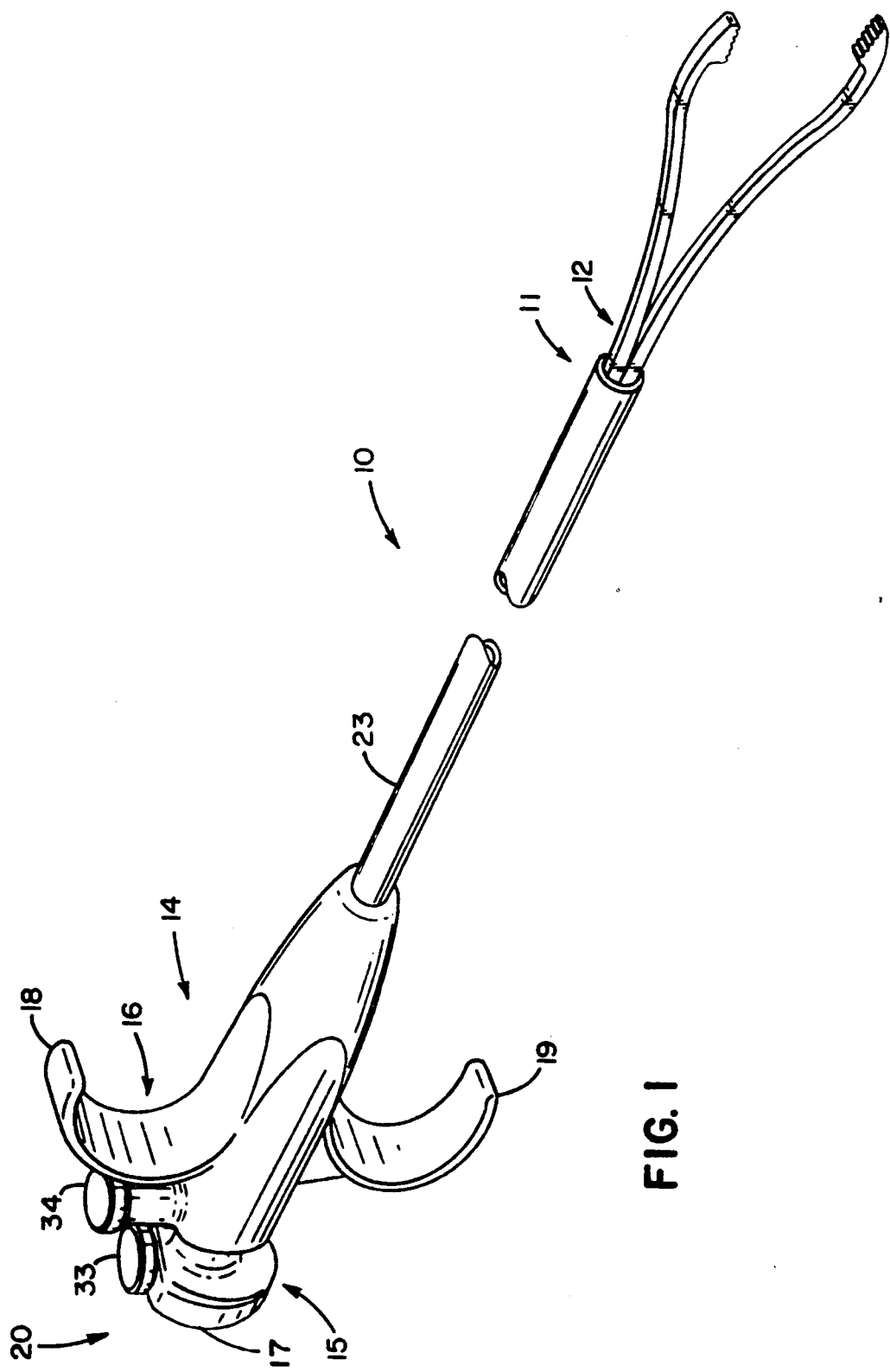
FIG. 1 is a perspective view of the assembled endoscopic grasping tool surgical instrument.

FIG. 1 is a perspective view of the endoscopic grasping surgical instrument 10. The anterior section 11 of the instrument 10 may house either a forceps jaw set 12 or a hemostat jaw set 13 depending upon intended usage. In FIG. 1 the forceps jaw set 12 is shown. In FIG. 1 the posterior section 20 of the instrument 10 includes the control handle structures generally designated 14. The control handle 14 is grasped by the surgeon and the anterior section 11 is inserted into the body cavity through a suitable port. In use, the surgeon operates the control handle 14 to manipulate the forceps jaw set 12. The instrument 10 is well suited to blunt dissection of tissues as well as grasping tissue pedicles and other structures.

The control handle 14 includes a rear grip structure 15 and a foregrip structure 16. In use the rear grip 15 and foregrip 16 are squeezed together to operate the instrument, The squeezing motion compresses a spring 22 which biases the jaw set into the closed position. The preferred rear grip is a pommel 17, while the preferred foregrip 16 comprises a pair of complimentary loops 18 and 19. These grip structures together form a symmetrical control handle 14. This symmetrical grip arrangement makes the instrument 10 operable with either the left or right hand. The symmetry also permits the instrument 10 to be operated in an upright position or an inverted position when rotated through 180 degrees. The assembly screws 33 and 34 provide the surgeon with a tactile and visual reference for the orientation of the forceps jaw set 12. The preferred semi-circular loops 18 and 19 may receive the forefinger and middle finger of the surgeon while the surgeon's thumb rests on the pommel 17. This preferred control handle 14 also can readily accept the surgeon's middle and ring finger on the loops 18 and 19 and palm on the pommel 17. This ambidextrous multi-position control handle 14 is also compact and light weight which materially aids the surgeon's control of the operating portion of the instrument. These preferred grip structures are preferably molded of medical grade polysulfone plastic molded onto a stainless steel tubular sheath 23.

Figure 2:
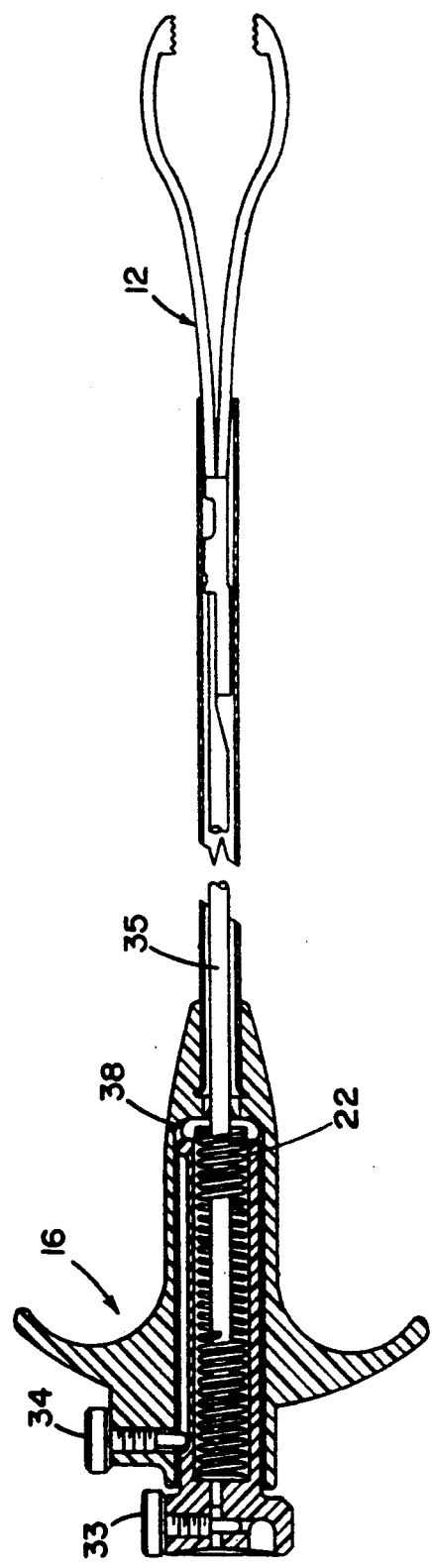
FIG. 2 is a crossection of the entire instrument depicting the control handle and the forceps jaw set in the extended and open position.

In FIG. 2 the instrument 10 is shown in cross-section with the forceps jaw structure in the open position. The cross-section view shows that the assembly screw 34 in the foregrip 16 holds the rear grip 15 in the foregrip 16 structure. Assembly screw 33 connects the rear grip 15 to one end of the connector rod 35. With the screws removed the connector rod 35 and attached forceps jaw set 12 can be removed, from the tubular sheath 23 by movement toward the anterior section 11 of the instrument. With the connector rod 35 removed, the jaw set can be detached from the connector rod 35. In general the forceps jaw set 12 or the hemostat jaw set 13 will form a disposable assembly which is discarded or cleaned after a single surgical use. Although any one of a number of connectors can be used to couple the forceps jaw set to the connector rod 35, the preferred connector is a plug-in-slot structure shown in FIG. 2 and FIG. 3. In embodiments where the entire tool is disposable, the assembly screws be replaced with pins preventing unauthorized disassembly.

The foregrip assembly 16 also contains a rubber gas seal 38 which encircles the circular control rod 35. This gas seal 38 prevents passage of fluid or gas through the instrument 10 and therefore maintains pneumoperitoneum, and sterility of the surgical field. In FIG. 2 the surgeon has squeezed the control handle 14 and compressed the spring 22 to extend the forceps jaw set 12 to the open position.

Figure 3:
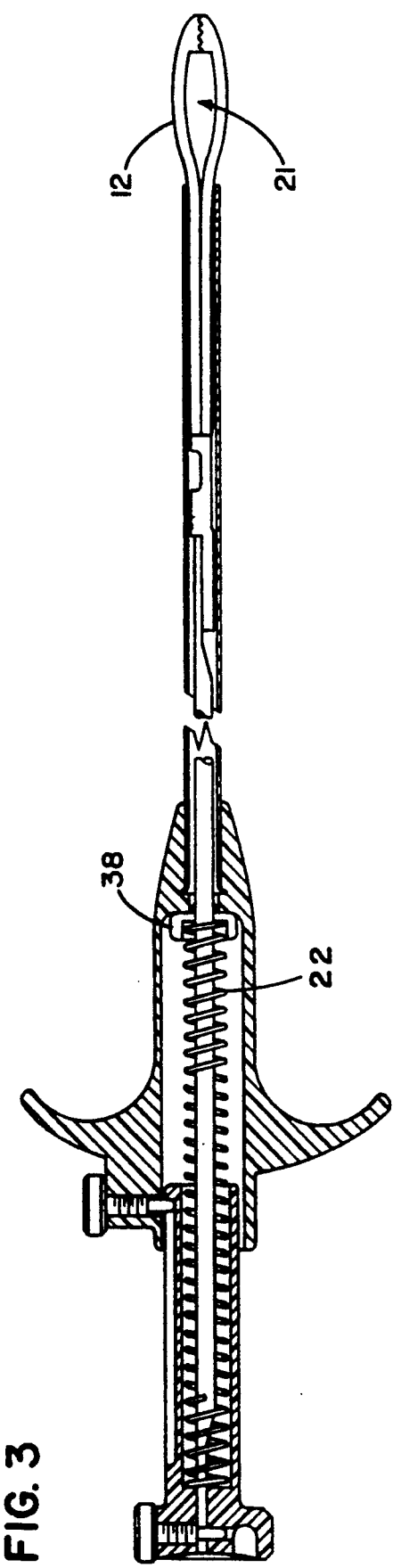
FIG. 3 is a crossection of the entire instrument depicting the control handle and the forceps jaw set in the retracted and closed position.
Figure 4:
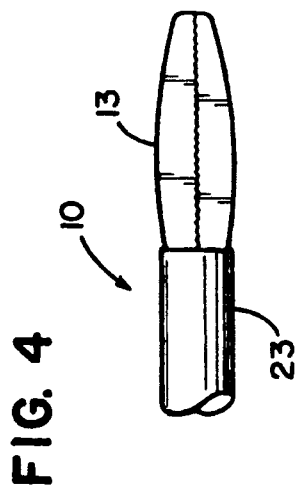
FIG. 4 is a view of the hemostat jaw set in the retracted and closed position.
Figure 5:
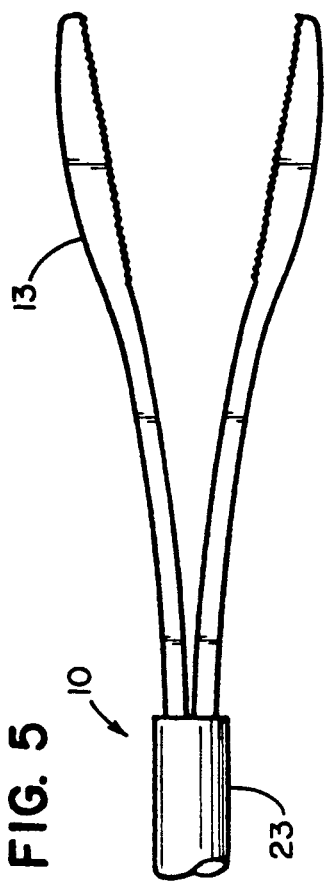
FIG. 5 is a view of the hemostat jaw set in the extended and open position.
Figure 6:
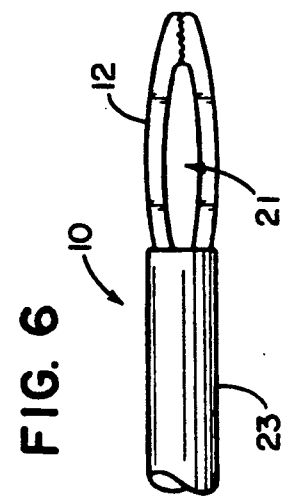
FIG. 6 is a view of the forceps jaw set in the retracted and closed position.
Figure 7:
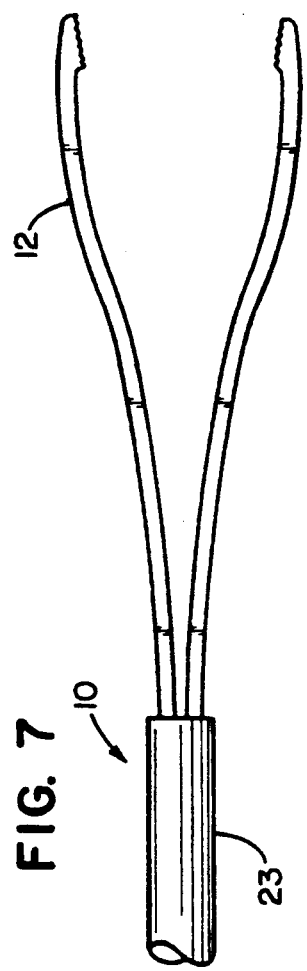
FIG. 7 is a view of the forceps jaw set in the extended and open position.

In FIG. 3 the surgeon has relaxed his grip on the control handle 14 to retract the forceps jaw set 12 to the closed position. With forceps jaws 12 positioned in the instrument 10, closure of the forceps jaw set 12 provides an aperture 21 for capturing tissues or other structures without squeezing them between the closed jaws. FIG. 6 shows an enlarged view of the forceps jaw set 12 in the retracted position. FIG. 7 shows a hemostat-type jaw set installed in the instrument 10. The hemostat jaw set 13 lacks an aperture. Therefore tissues or other structures captured by retraction of the jaws are compressed or clamped between the jaws. This hemostat jaw set 13 may be used to close off vessels during cautery or ligation procedures. While the forceps jaw set 12 may be used to capture and control tissues or ligatures. Although the two types of jaw set are readily interchangeable, the surgeon will typically have several instruments configured in each form during a typical laparoscopic surgery.

Figure 8:
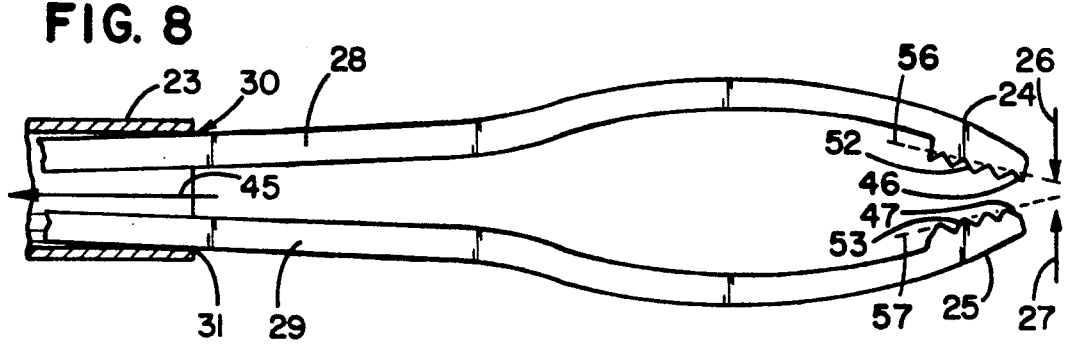
FIG. 8 is an enlarged and exaggerated scale, crossection of the forceps jaw set depicting the interaction between the jaws during closure.
Figure 9:
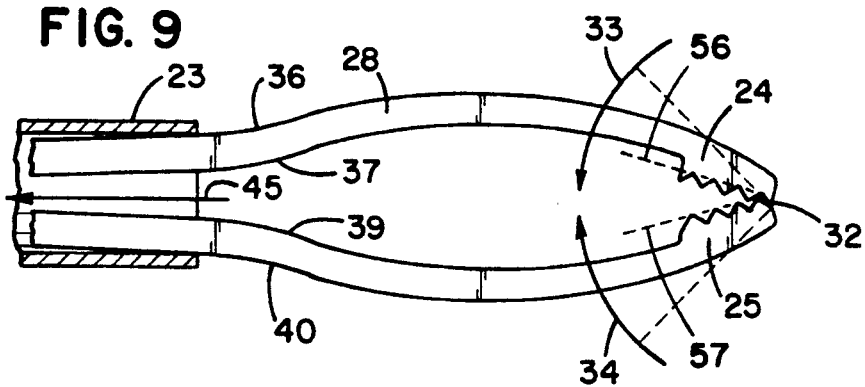
FIG. 9 is an enlarged and exaggerated scale, crossection of the forceps jaw set depicting the interaction between the jaws during closure.
Figure 10:
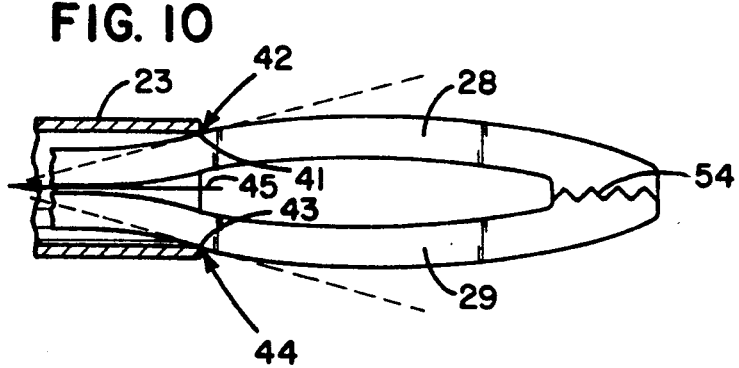
FIG. 10 is an enlarged and exaggerated scale, crossection of the forceps jaw set depicting the interaction between the jaws during closure.

FIGS. 8-10 should be considered together. Collectively they depict the progressive stages of retraction and have been drawn in exaggerated form to more clearly show the sequence of closure. Although the forceps jaw set 12 configuration has been shown for clarity the hemostat jaw set 13 operates in an identical manner.

FIG. 8 shows the first jaw member 24 and the second jaw member 25 being moved together as indicated by line 26 and line 27. In this view it can be seen that the first jaw face 52 is not parallel to the second jaw face 53 as the first jaw member 24 approaches the second jaw member 25. This motion of the jaw members results from movement of the jaw arm 27 and jaw arm 28 into the tubular sheath 23 as indicated by line 45. During this motion the tubular sheath 23 contacts the first jaw ar 28 at the end of the tubular sheath 23 indicated by point of contact 30 and contacts the second jaw arm 29 at point of contact 31.

FIG. 9 shows the distal first tip 46 of the first jaw member 24 touching the distal second tip 47 of the second jaw member at a point of contact forming a jaw closure pivot point. At this point the plane 56 (FIG. 8-9) of the first jaw face 52 and the plane 57 (FIG. 8-9) of the second jaw face 53 intersect and form an acute angle 58 (FIG. 9) with respect to the pivot point 32. Once the jaw closure pivot point 32 is established by actual contact or proximate contact with tissue, the first jaw member 24 and the second jaw member 25 rotate about this jaw closure pivot point 32 to further close the jaws. This rotational motion of the first jaw member 24 is depicted by reference line 33, and is depicted by reference line 34 for the second jaw member 25. The rotational motion places the outer surface 36 of the first jaw arm 28 in compression and the inner surface 37 of the first jaw arm 28 in tension. In a complimentary fashion the inner surface 39 of the second jaw arm 29 is placed into tension and the outer surface 40 of the second jaw arm 29 is placed in compression.

FIG. 10 shows further retraction of the jaw set in to the sheath a shows how the inclined outer surface 41 of the first jaw arm engages the tubular sheath 23 at point of contact 42. Reference line 45 approximates the inclination of surface 41 at point 42. In a complimentary fashion the second jaw arm 29 also has an inclined surface 43 forming a point of contact 44 with the tubular sheath 23 With the jaws completely closed into substantial conformity 54. As shown in FIG. 10 the jaw pressure between first jaw face 52 and second jaw face 53 is approximately uniform and in excess of prior art hinged jaw structures.

Figure 11:
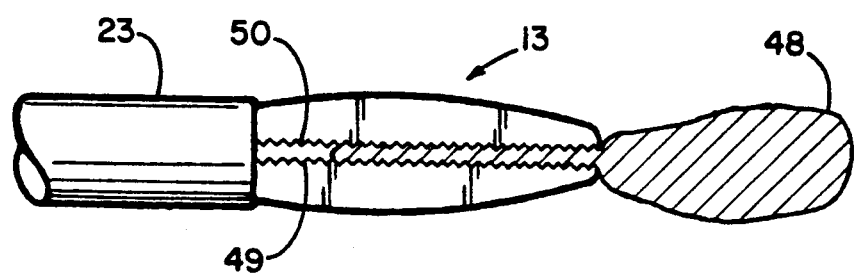
FIG. 11 is a view of the hemostat jaw set closed on an anatomic structure.
Figure 12:
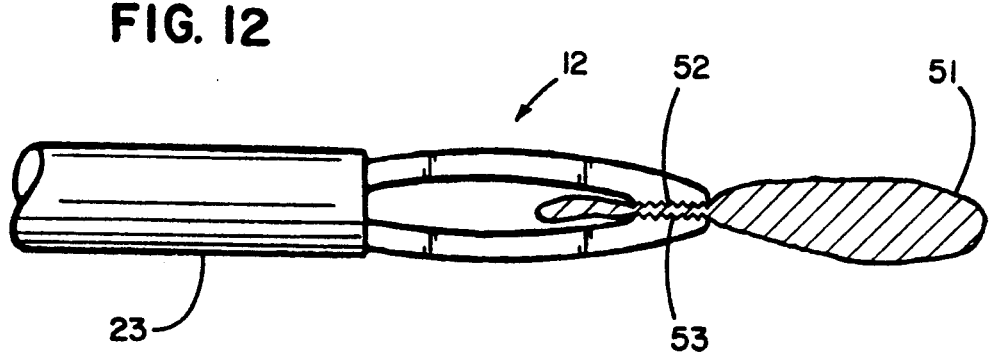
FIG. 12 is a view of the forceps jaw set closed on an anatomic structure.

The illustrative FIGS. 8-10 show operation were there is no anatomical structure or other object between the faces of the jaws. In FIG. 11 a mass of tissue 48 is located between jaw face 49 and jaw face 50 of the hemostat jaw set 13. While in FIG. 12 a mass of tissue 51 is positioned between jaw face 52 and jaw face 53. The presence of the tissue masses prevents the distal tips from contacting each other but it does place the tips into proximate contact and therefor does not alter the operation of the jaws during closure.

Although the illustrative jaw sets 12 and 13 depicted herein are formed from a unitary piece of metal or other material it should be appreciated that the jaws could be hinged together near their attachment point with the connector rod 35. Similarly, the preferred arms are of uniform crossection along their entire length, except at the jaws themselves however it should be appreciated that the this crossection may be varied along the length of the arms as well. In a similar fashion the tubular sheath and the connecting rod are shown with a circular cross-section to facilitate sealing with the port and sealing with gas seal 38, however non circular cross-sections are operable as well. Although the two jaw sets depicted herein are believed to be the most useful configurations for general surgery, the number of jaw arms and jaw members may be increased in accordance with the teaching of this disclosure without departing from the scope of the invention.

What is claimed is:
1. An endoscopic grasping tool surgical instrument comprising:
   a control handle;
   a tubular sheath coupled to said control handle;
   a connector rod coupled to said control handle, and adapted for reciprocating motion within said tubular sheath in response to control handle motion;
   a first jaw arm, having a first jaw member;
   said first jaw member having a first jaw face, said first jaw face defining a first jaw face plane;
   a second jaw arm, having a second jaw member;
   said second jaw member having a second jaw face, said second jaw face defining a second jaw face plane;
   said first and second jaw arms being coupled to said connector rod, and adapted to be moved to an open position by motion of said connector rod, and adapted to be moved to a closed position, by motion of said connector rod, said closed position defined by said first jaw face in substantial conformity with said second jaw face;

said first jaw member having a distal first tip;

said second jaw member having a distal second tip;

said first distal tip being aligned with said second distal tip such that motion of said connector rod moves said first distal tip toward said second distal tip, establishing proximate contact between said first distal tip and said second distal tip, and thereby defining a jaw closure pivot point with said first jaw face plane and said second jaw face plane forming an acute angle with said jaw closure pivot point;

and whereby, continued motion of said first jaw member and said second jaw member toward said closed position causes said first jaw member and said second jaw member to close by rotational motion about said jaw closure pivot point.

2. The endoscopic grasping tool surgical instrument of claim 1 wherein:

said first jaw arm has an inclined surface brought into contact with said tubular sheath during closure;

said second jaw arm has an inclined surface brought into contact with said tubular sheath during closure;

whereby, abutment of said first and second arms with said sheath causes said first jaw member and said second jaw member to move toward said closed position and rotation of said first jaws face and said second jaw face about said jaw closure pivot point bringing said first and second jaw faces into substantial conformity.

3. The endoscopic grasping tool surgical instrument of claim 2 wherein:

said first jaw arm has a first jaw face extending from the end of said tubular sheath to said distal first tip when said first and second jaw faces are closed into conformity;

said second jaw arm has a second jaw face extending from the end of said tubular sheath to said distal second tip when said first and second jaw faces are closed into conformity;

thereby, creating a clamping surface for compressing structures.

4. The endoscopic grasping tool surgical instrument of claim 2 wherein:

said first jaw arm has a first jaw face extending from a position intermediate between the end of said tubular sheath to said distal first tip when said first and second jaw faces are closed into conformity;

said second jaw arm has a second jaw face extending from a position intermediate between the end of said tubular sheath to said distal second tip when said first and second jaw faces are closed into conformity;

thereby, creating an aperture for capturing structures.

5. The endoscopic grasping tool surgical instrument of claim 1 wherein:

said control handle includes a foregrip and a rear grip, said foregrip including a pair of semicircular finger reception loops, and said rear grip including a pommel.

6. The endoscopic grasping tool surgical instrument of claim 1 further comprising:

a gas seal located in said sheath surrounding said control rod, whereby gas leakage through said instrument is minimized.

7. An endoscopic grasping tool surgical instrument comprising:

a control handle having a foregrip and having a rear grip, said foregrip including a pair of semicircular finger reception loops, and said rear grip including a pommel;

a tubular sheath, having a generally circular cross-section and having a generally cylindrical exterior shape, and having a generally circular cross-section interior lumen, coupled to said control handle;

a connector rod coupled to said control handle, and adapted for reciprocating motion within said tubular sheath in response to control handle motion;

a gas seal located within said sheath and in contact with said sheath and in contact with said control rod, whereby fluid exchange through said sheath is prevented;

a first jaw arm, having a first jaw member;

said first jaw member having a first jaw face, said first jaw face defining a first jaw face plane;

a second jaw arm, having a second jaw member;

said second jaw member having a second jaw face, said second jaw face defining a second jaw face plane;

said first and second jaw arms being coupled to said connector rod, and adapted to be moved to an open position by motion of said connector rod, and adapted to be moved to a closed position, by motion of said connector rod, said closed position defined by said first jaw face in substantial conformity with said second jaw face;

said first jaw member having a distal first tip;

said second jaw member having a distal second tip;

said first distal tip being aligned with said second distal tip such that motion of said connector rod moves said first distal tip toward said second distal tip, establishing proximate contact between said first distal tip and said second distal tip, and thereby defining a jaw closure pivot point with said first jaw face plane and said second jaw face plane forming an acute angle with said jaw closure pivot point;

and whereby, continued motion of said first jaw member and said second jaw member toward said closed position causes said first jaw member and said second jaw member to close by rotational motion about said jaw closure pivot point.

* * * * *

UNITED STATES PATENT AND TRADEMARK OFFICE
CERTIFICATE OF CORRECTION

PATENT NO. : 5,222,973

DATED : June 29, 1993

INVENTOR(S) : Leslie A. Sharpe, et al

Page 1 of 2

It is certified that error appears in the above-indentified patent and that said Letters Patent is hereby corrected as shown below:

In column 1, line 59, please delete the word "crossection" and insert therefor --cross-section--

In column 1, line 62, please delete the word "crossection" and insert therefor --cross-section--

In column 2, lines 5 and 6, please delete the word "crossection" and insert therefor --cross-section--

In column 2, lines 8 and 9, please delete the word "crossection" and insert therefor --cross-section--

In column 2, lines 11 and 12, please delete the word "crossection" and insert therefor --cross-section--

In column 2, line 41, please delete the word "complimentary" and insert therefor --complementary--

In column 3, line 10, please place quotation marks around "plug-in-slot"

In column 3, line 56, please delete "ar" and insert therefor --arm--

UNITED STATES PATENT AND TRADEMARK OFFICE
CERTIFICATE OF CORRECTION

PATENT NO. : 5,222,973

DATED : June 29, 1993

INVENTOR(S) : Leslie A. Sharpe, et al

It is certified that error appears in the above-indentified patent and that said Letters Patent is hereby corrected as shown below:

In column 3, lines 63 and 64, please delete (FIG. 8-9) and insert therefor --(FIGS. 8-9)--

In column 3, line 64, please delete (FIG. 8-9) and insert therefor --(FIGS. 8-9)--

In column 4, line 8, please delete the word "complimentary" and insert therefor --complementary--

In column 4, lines 12 and 13, please delete "in to the sheath a" and insert therefor --into the sheath and--

In column 4, line 16, please delete the word "complimentary" and insert therefor --complementary--

In column 4, line 39, please delete the word "crossection" and insert therefor --cross-section--

In column 4, line 41, please delete the word "crossection" and insert therefor --cross-section--

Signed and Sealed this

Fifth Day of April, 1994

Attest:

BRUCE LEHMAN

*Attesting Officer*    Commissioner of Patents and Trademarks